(12) United States Patent
Schwarz

(10) Patent No.: US 9,629,506 B1
(45) Date of Patent: Apr. 25, 2017

(54) DENTAL HYGIENE STORAGE DEVICE

(71) Applicant: Wilhelm Schwarz, Lebanon, PA (US)

(72) Inventor: Wilhelm Schwarz, Lebanon, PA (US)

( * ) Notice: Subject to any disclaimer, the term of this patent is extended or adjusted under 35 U.S.C. 154(b) by 0 days.

(21) Appl. No.: 15/091,140

(22) Filed: Apr. 5, 2016

Related U.S. Application Data

(60) Provisional application No. 62/287,014, filed on Jan. 26, 2016.

(51) Int. Cl.
*A47K 1/09* (2006.01)
*A61C 15/04* (2006.01)

(52) U.S. Cl.
CPC .............. *A47K 1/09* (2013.01); *A61C 15/043* (2013.01)

(58) Field of Classification Search
CPC .......... A47K 1/09; A47K 10/22; A47K 17/00; A47K 11/10; A61C 15/043
USPC .......................................................... 211/65
See application file for complete search history.

(56) References Cited

U.S. PATENT DOCUMENTS

| | | | | | |
|---|---|---|---|---|---|
| 338,402 | A | * | 3/1886 | Griswold ................. | A47K 1/09 211/1 |
| 1,615,571 | A | * | 1/1927 | Crecelius ................. | A47K 1/09 132/308 |
| 1,711,327 | A | * | 4/1929 | Rock ........................ | A47K 1/09 132/310 |
| 1,713,379 | A | * | 5/1929 | Fromwiller .............. | A47K 1/09 132/310 |
| 1,955,736 | A | * | 4/1934 | Claytor .................... | A47K 1/09 132/310 |
| 2,576,303 | A | * | 11/1951 | Matter .................... | A47G 25/02 132/314 |
| 2,967,651 | A | * | 1/1961 | Zackheim ............... | A47F 13/04 225/80 |
| 3,194,621 | A | * | 7/1965 | Frost ....................... | A47K 1/09 312/206 |
| 3,531,072 | A | * | 9/1970 | Lindquist ................. | A47K 1/09 211/65 |
| 3,894,550 | A | | 7/1975 | Eaton | |
| 4,140,222 | A | * | 2/1979 | Francavilla ............... | A47K 1/09 211/65 |
| 4,566,597 | A | * | 1/1986 | Caputo .................... | A47K 1/09 108/152 |
| 5,054,674 | A | * | 10/1991 | Fortman .................. | A47K 1/09 225/42 |
| 5,680,933 | A | | 10/1997 | Miller | |
| 2003/0024546 | A1 | | 2/2003 | Linttell | |
| 2004/0050733 | A1 | | 3/2004 | Page et al. | |
| 2011/0133611 | A1 | | 6/2011 | Clarke et al. | |

* cited by examiner

*Primary Examiner* — Korie H Chan
(74) *Attorney, Agent, or Firm* — Global Intellectual Property Agency, LLC; Daniel Boudwin

(57) ABSTRACT

A dental hygiene storage device for use in organizing and storing one or more toothbrushes, tubes of toothpaste, and dental floss. The dental hygiene storage device includes a base having an upstanding panel thereon, wherein the base is configured to rest on a horizontal support surface, such as a sink or countertop. The upstanding panel includes a toothbrush holder thereon for use in holding one or more toothbrushes in a vertical orientation. The base has one or more recesses for use in holding a portion of a tube of toothpaste therein. Further, the base includes a compartment in which dental floss can be stored, wherein the compartment is removably covered via a lid and includes an opening through which the floss may extend.

7 Claims, 2 Drawing Sheets

DENTAL HYGIENE STORAGE DEVICE

CROSS REFERENCE TO RELATED APPLICATION

This application claims the benefit of U.S. Provisional Application No. 62/287,014 filed on Jan. 26, 2016. The above identified patent application is herein incorporated by reference in its entirety to provide continuity of disclosure.

BACKGROUND OF THE INVENTION

Field of the Invention

The present invention relates to dental hygiene storage devices. More specifically, the present invention provides a storage device for holding one or more toothbrushes, one or more toothpaste tubes, and dental floss.

It is important to exercise proper dental hygiene in order to prevent staining, formation of cavities, gum disease, and other similar dental problems. In order to maintain proper dental health many people regularly brush their teeth with a toothbrush and toothpaste. Further, it is also important to utilize tooth floss in order to remove food that has become stuck between adjacent teeth. However, it can be difficult to properly store and organize these various items in a convenient manner. This is particularly true for bathrooms used by several people which may require the storage and organization of several toothbrushes, tubes of toothpaste, and other dental hygiene accessories.

Some people simply rest their toothbrush adjacent to a sink when the toothbrush is not in use. However, the sink may have germs and bacteria thereon if it is not frequently and thoroughly cleaned. Further, the sink or counter area may have insufficient space for storing the toothbrush, toothpaste, and floss. As a result, these items may be stored in various places, which can be inconvenient as the user must individually locate and find each item. Thus, an improved dental hygiene storage device is desired.

Devices have been disclosed in the prior art that relate to dental hygiene storage and organizing devices. These include devices that have been patented and published in patent application publications. These devices generally relate to dental hygiene holding devices having various configurations for storing toothbrushes and other items, such as U.S. Published Patent Application Number 2004/0050733, U.S. Published Patent Application Number 2003/0024546, U.S. Pat. No. 5,680,933, U.S. Published Patent Application Number 2011/0133611, and U.S. Pat. No. 3,894,550.

These prior art devices have several known drawbacks. The devices in the prior art fail to provide a means for storing dental floss therein that allows the user to easily dispense and use the dental floss. Further, the prior art devices fail to provide removable holders that allow the user to customize the configuration thereof.

In light of the devices disclosed in the prior art, it is submitted that the present invention substantially diverges in design elements from the prior art and consequently it is clear that there is a need in the art for an improvement to existing dental hygiene storage devices. In this regard the instant invention substantially fulfills these needs.

SUMMARY OF THE INVENTION

In view of the foregoing disadvantages inherent in the known types of dental hygiene storage devices now present in the prior art, the present invention provides a new dental hygiene storage devices wherein the same can be utilized for providing convenience for the user when storing and organizing dental hygiene products.

The present invention provides a dental hygiene storage device for use in storing and organizing toothbrushes, toothpaste, and dental floss, among other related items. The storage device comprises a base having an upstanding panel extending therefrom. The upstanding panel comprises a toothbrush holder thereon for holding one or more toothbrushes in a vertical orientation. The base comprises one or more recesses for storing a portion of a tube of toothpaste therein. Further, the base comprises a compartment in which dental floss may be stored, wherein the compartment comprises a slot through which a portion of the dental floss can be threaded.

Other objects, features and advantages of the present invention will become apparent from the following detailed description taken in conjunction with the accompanying drawings.

BRIEF DESCRIPTIONS OF THE DRAWINGS

Although the characteristic features of this invention will be particularly pointed out in the claims, the invention itself and manner in which it may be made and used may be better understood after a review of the following description, taken in connection with the accompanying drawings wherein like numeral annotations are provided throughout.

DETAILED DESCRIPTION OF THE INVENTION

Figure 1:
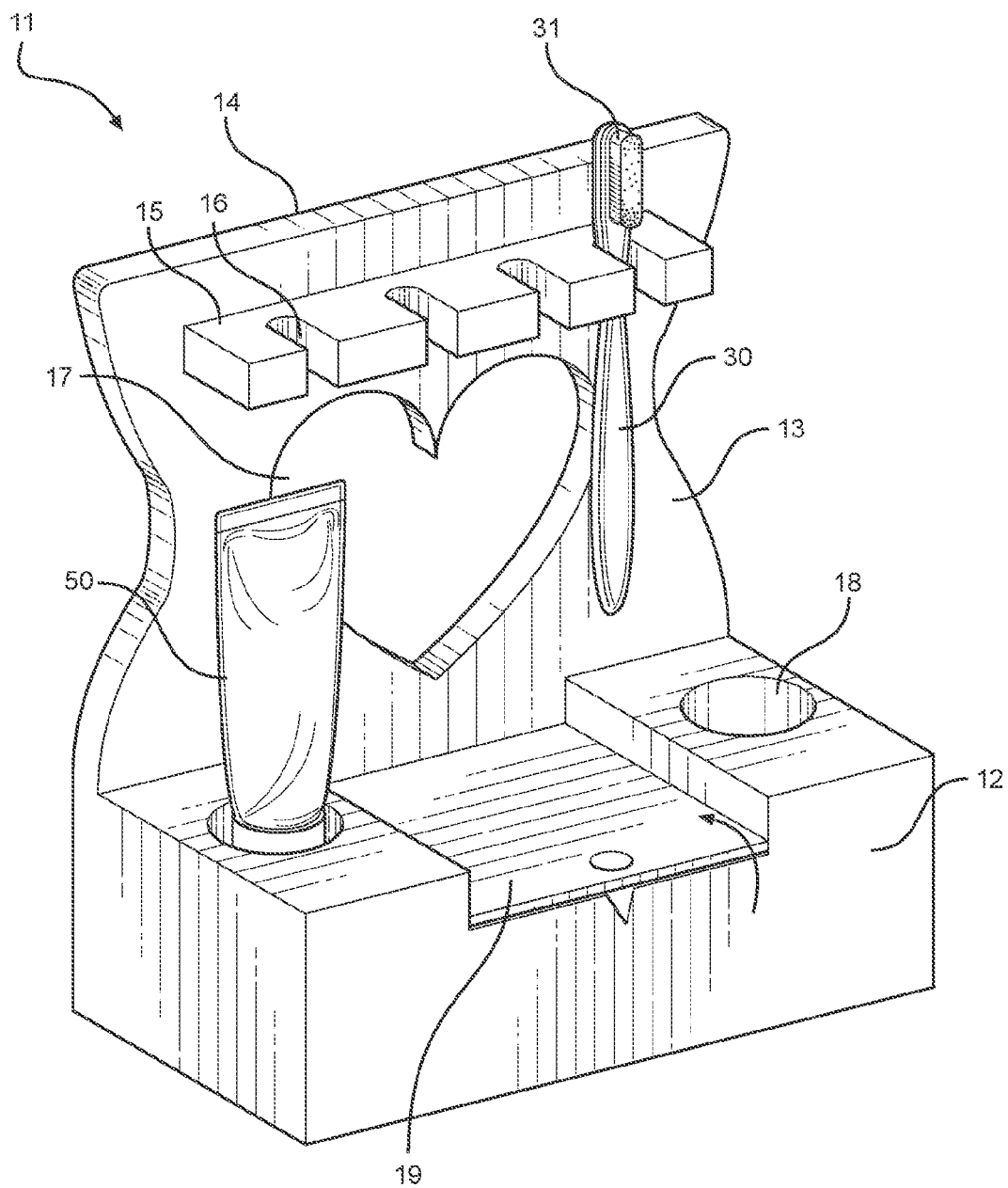
FIG. 1 shows a front perspective view of the dental hygiene storage device.

Reference is made herein to the attached drawings. Like reference numerals are used throughout the drawings to depict like or similar elements of the dental hygiene storage device. For the purposes of presenting a brief and clear description of the present invention, the preferred embodiment will be discussed as used for storing and organizing various types of dental hygiene products, such as toothbrushes, toothpaste tubes, dental floss, and the like. The figures are intended for representative purposes only and should not be considered to be limiting in any respect.

Referring now to FIG. 1, there is shown a front perspective view of the dental hygiene storage device. The dental hygiene storage device 11 comprises a base 12 having an upstanding panel 13 extending therefrom. The upstanding panel 13 extends vertically upward from the base 12 at a rear portion thereof. The dental hygiene storage device 11 can be positioned on a horizontal support surface such as a counter or sink, wherein the base 12 stabilizes the storage device 11 in an upright orientation. Alternatively, the user can affix the rear of the upstanding panel 13 to a vertical support surface, such as a wall, for securing the storage device 11 thereon. The upstanding panel 13 can be affixed to a wall via any conventional fastening methods such as by use of adhesives, fasteners such as screws, bolts, or nails, or via brackets.

The upstanding panel 13 comprises a toothbrush holder 15 on a front surface thereof. The toothbrush holder 15 comprises one or more grooves 16 adapted to removably receive a portion of a toothbrush 30 therein. The grooves 16 are sized so as to frictionally hold the toothbrush 30 therein. The grooves 16 are further sized so as to prevent the head 31 of the toothbrush 30 from passing therethrough. In this way, the toothbrush holder 15 can be used to store one or more toothbrushes 30 in a vertical orientation. The toothbrush holder 15 is preferably located adjacent to the upper end 14 of the upstanding panel 13 so that the toothbrushes 30 can be suspended by the storage device 11 without the toothbrush 30 contacting the base 12 of the storage device 11.

The upstanding panel 13 further has a central cutout 17 thereon. The cutout 17 provides a decorative appearance and adds visual interest to the upstanding panel 13. The cutout 17 may have any of various shapes, and in the illustrated embodiment the cutout 17 resembles a heart. In alternate embodiments, the cutout 17 resembles a letter or initials thereon, among other symbols or indicia.

The base 12 comprises one or more recessed areas 18 thereon. In the illustrated embodiment, the recessed areas 18 are shown as having circular openings. The recessed areas 18 are preferably positioned on opposing sides of the base 12. The recessed areas 18 can removably receive a portion of a tube of toothpaste 50 therein so as to support the toothpaste 50 in an upstanding, vertical orientation. This allows for the toothpaste 50 to be easily accessed. The recessed areas 18 are positioned so that the toothpaste 50 does not contact or interfere with the toothbrushes 30 supported by the toothbrush holder 15.

The base 12 further comprises a compartment in which dental floss can be stored. The compartment has a lid 19 pivotally or removably secured thereon so as to enclose the dental floss therein. Preferably, the compartment is positioned centrally on the base 12 so that it is positioned in between the recessed areas 18 on the base 12.

Figure 2:
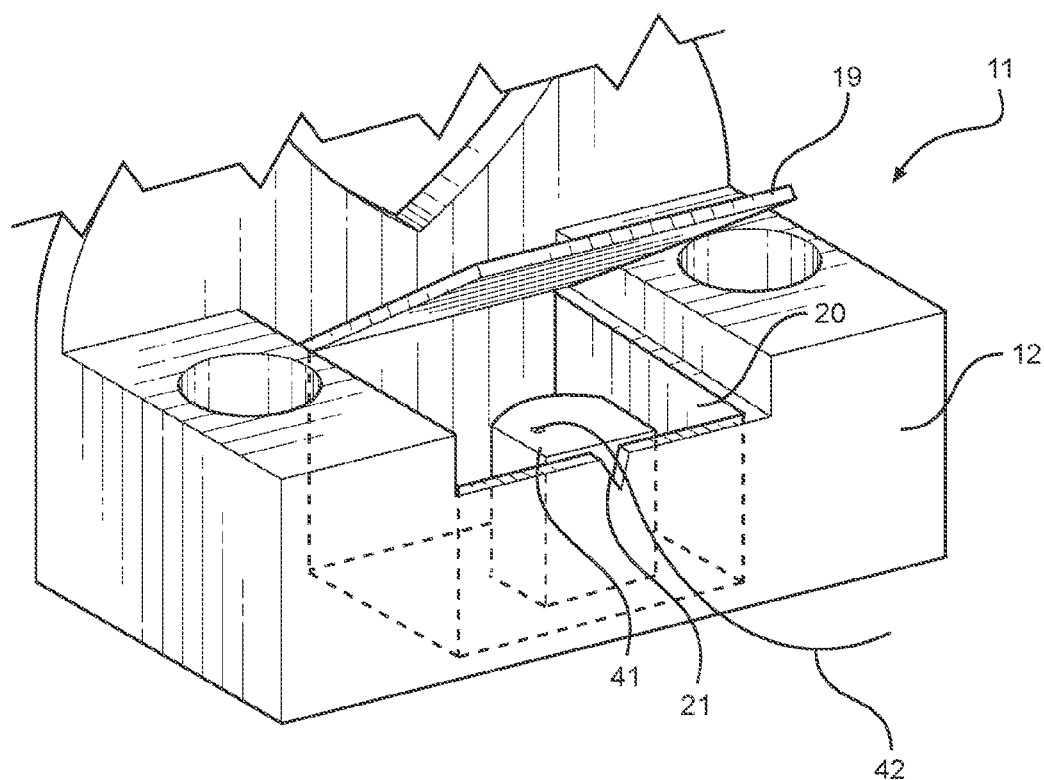
FIG. 2 shows a close-up view of the base of the dental hygiene storage device.

Referring now to FIG. 2, there is shown a close-up view of the base of the dental hygiene storage device. The compartment 20 has an interior volume adapted to receive a dental floss dispenser 41 therein. Any of various types of conventional dental floss dispensers 41 can be positioned within the compartment 20. Once the dental floss dispenser 41 is deposited into the compartment 20, the user can close the lid 19 to enclose the dental floss dispenser 41 therein. A slot 21 is positioned on a front surface of the base 12 wherein the slot 21 allows a portion of the floss 42 to pass therethrough. The slot 21 preferably has a sharpened edge so as to be used to cut the floss 42 when desired. In this way, the user can pull the floss 42 to a desired length and can then cut the floss 42 by pulling the floss 42 against the edge of the slot 21.

Figure 3:
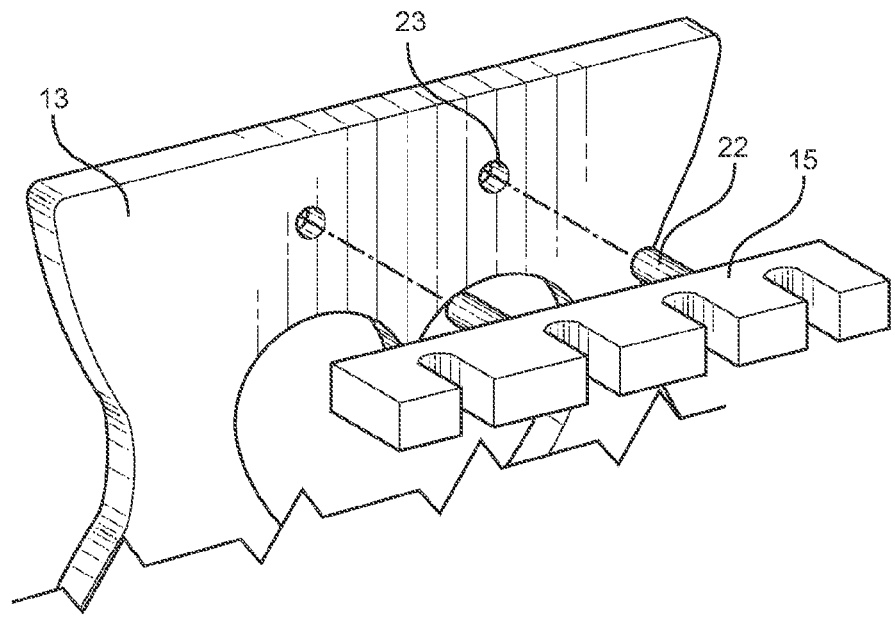
FIG. 3 shows a close-up view of the toothbrush holder of the dental hygiene storage device.

Referring now to FIG. 3, there is shown a close-up view of the toothbrush holder of the dental hygiene storage device. In some embodiments, the toothbrush holder 15 is removably affixed to the upstanding panel 13. The toothbrush holder 15 comprises one or more pegs 22 thereon that are adapted to be inserted into apertures 23 on the upstanding panel 13 in order to secure the toothbrush holder 15 to the upstanding panel 13. In this way, the user can easily install and remove the toothbrush holder 15 for cleaning. Further, the toothbrush holder 15 can be interchanged with other toothbrush holders 15 having differing numbers of grooves 16 thereon. Further, in some embodiments, a toothbrush holder 15 includes various shaped grooves 16 for securing different types of toothbrushes and other dental hygiene tools.

It is therefore submitted that the instant invention has been shown and described in what is considered to be the most practical and preferred embodiments. It is recognized, however, that departures may be made within the scope of the invention and that obvious modifications will occur to a person skilled in the art. With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A dental hygiene storage device, comprising:
   a base having an upstanding panel extending therefrom;
   a toothbrush holder affixed to the upstanding panel, wherein the toothbrush holder is adapted to store one or more toothbrushes in a vertical orientation;
   the base having a compartment and a pair of recessed areas, wherein the pair of recessed areas are disposed on opposing sides of the base and the compartment is positioned therebetween; wherein the compartment having a lid pivotally affixed thereto, the compartment adapted for storage of dental floss therein;
   wherein each of the recessed areas are enclosed having an opening configured to receive a tube of toothpaste therein.

2. The dental hygiene storage device of claim 1, wherein the compartment further comprises a slot on a front portion thereof, wherein the slot is adapted to allow a portion of the dental floss to extend therethrough.

3. The dental hygiene storage device of claim 2, wherein the slot has sharpened edges.

4. The dental hygiene storage device of claim 1, wherein the pair of recessed areas have circular openings.

5. The dental hygiene storage device of claim 1, wherein the toothbrush holder comprises one or more grooves thereon adapted to removably secure a portion of a toothbrush therein via frictional fit.

6. The dental hygiene storage device of claim 1, wherein the toothbrush holder is removably securable to the upstanding panel.

7. The dental hygiene storage device of claim 1, wherein the upstanding panel extends from a rear portion of the base.

* * * * *